United States Patent

Angell et al.

[11] 3,983,581
[45] Oct. 5, 1976

[54] HEART VALVE STENT

[75] Inventors: William W. Angell, San Jose, Calif.;
David L. Yoon, East Lansing, Mich.

[73] Assignee: William W. Angell, San Jose, Calif.

[22] Filed: Nov. 17, 1975

[21] Appl. No.: 632,309

Related U.S. Application Data

[63] Continuation-in-part of Ser. No. 536,300, Jan. 20, 1975, abandoned.

[52] U.S. Cl. .................................................. 3/1.5
[51] Int. Cl.² ........................................... A61F 1/22
[58] Field of Search .................................... 3/1.5, 1

[56] References Cited
UNITED STATES PATENTS

| | | | |
|---|---|---|---|
| 3,548,418 | 12/1970 | Angell et al | 3/1.5 |
| 3,570,014 | 3/1971 | Hancock | 3/1.5 |
| 3,727,240 | 4/1973 | Child | 3/1.5 |
| 3,755,823 | 9/1973 | Hancock | 3/1.5 |

OTHER PUBLICATIONS

"Heart Valve Replacement With Reinforced Aortic Heterografts" by M. I. Ionescu et al, *The Journal of Thoracic & Cardiovascular Surgery*, vol. 56, No. 3, Sept. 1968, pp. 333-350.

"Pig Aortic Valve as a Replacement for the Mitral-Valve in the Dog" by W. A. Reed et al, The Journal of Thoracic & Cardiovascular Surgery, vol. 57, No. 5, May 1969, pp. 663-667.

*Primary Examiner*—Ronald L. Frinks
*Attorney, Agent, or Firm*—Thomas E. Ciotti

[57] ABSTRACT

An anatomically configured stent for a tanned, expanded natural tissue heart valve and a valve prosthesis including the stent are disclosed. The stent comprises a frame whose interior configuration is the anatomical negative of the exterior configuration of a tanned, expanded, natural tissue valve and a fabric cover covering at least the exterior of the frame, the cover having a bead along its perimeter that provides a site for attachment of the valve to the stent.

24 Claims, 17 Drawing Figures

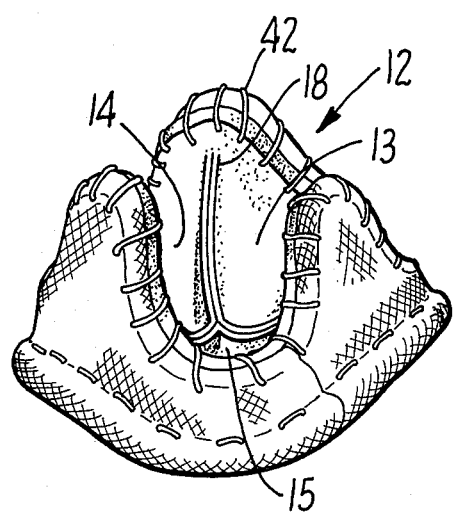
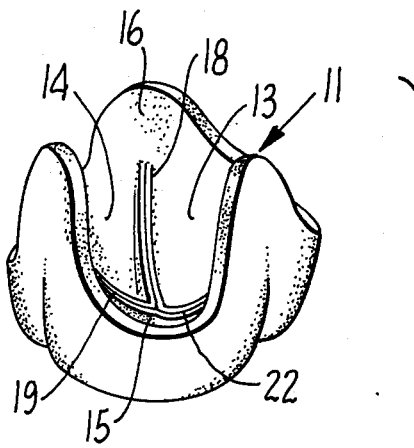
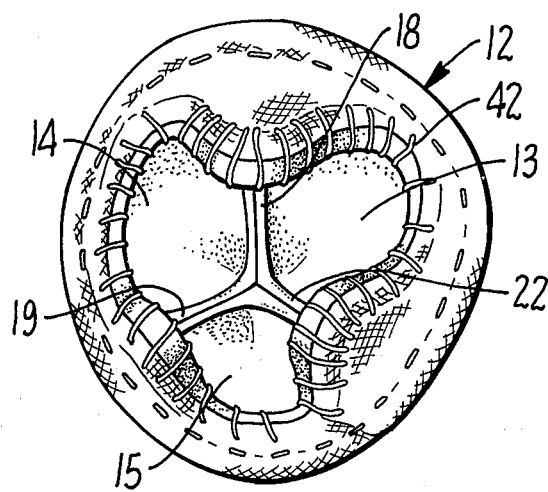
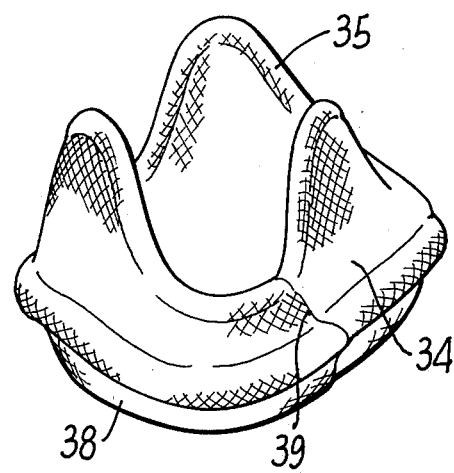
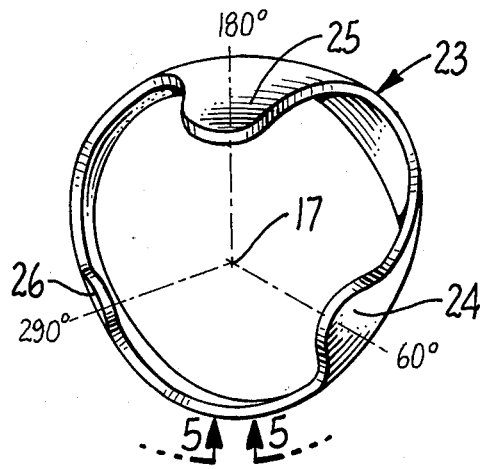
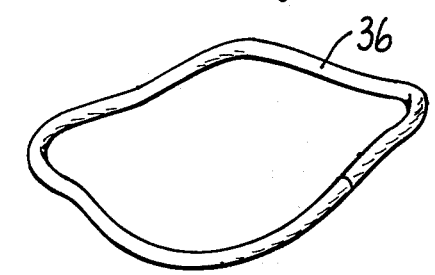
FIG. 1.
FIG. 2.
FIG. 3.
FIG. 4.

HEART VALVE STENT

CROSS-REFERENCE TO RELATED APPLICATION

This application is a continuation-in-part of application Ser. No. 536,300, filed 20 Jan. 1975, now abandoned.

BACKGROUND OF THE INVENTION

1. Field of the Invention

This invention relates to a stent for tanned, natural tissue heart valves and to a heart valve prosthesis including the stent.

2. Description of the Prior Art

There are basically two types of heart valve prostheses: mechanical valve prostheses and natural tissue valve prostheses. Recent experience indicates the tissue type may be superior to the mechanical type as regards similarity to natural flow characteristics, thrombogenicity and incidence of catastrophic in vivo dysfunction.

It is known that the tensile properties and antigenic reaction of natural tissue valves may be improved if they are tanned before being implanted. Glutaraldehyde has been used as a tanning agent. (Yarbrough et al: Structural alterations in tissue cardiac valves implanted in patients and in calves. *J Thoracic and Cardiovascular Surgery* 65, March 1973, pp 364–74.)

Heart valve prostheses desirably include a stent or support in which the valve is held in place. The stents normally comprise a frame covered with a cloth or sponge sleeve. Variously configured frames and frame materials have been used in an attempt to provide a stent that does not contribute to in vivo valve dysfunction. For instance U.S. Pat. No. 3,570,014 discloses a stent made of an annular bendable tubular framework, portions of which are covered with fabric to provide an attachment site for the valve. The frame is bent to fit the valve. Another tubular framework stent is disclosed in U.S. 3,755,823. That stent is made of spaced annular tube members that carry three deflectable posts. The framework is covered with a fabric sleeve. Carpentier (*Human Organ Support and Replacement: Transplantation and Artificial Prostheses*. J Hardy, ed, Springfield, Ill, Charles C Thomas, 1971, pp 332–62) reports stented valves in which an attempt was made to make the stent frames anatomical by dimensioning them according to measured inside valve dimensions. Even so, these prior art stents were only partial or poor facsimilies of a truly anatomically configured stent.

SUMMARY OF THE INVENTION

The invention is an anatomically configured stent for a natural, tissue heart valve that has been tanned and expanded simultaneously with glutaraldehyde at a positive pressure and a heart valve prosthesis comprising such a valve affixed within the stent. The stent comprises: a plastic frame the inner configuration of which is substantially identical to the exterior configuration of the tanned, expanded valve; and a fabric cover covering at least the exterior surface of the frame, said cover having means along its perimeter providing a site for attachment of the valve to the stent.

The basic features that distinguish the invention stent from prior art stents are: (1) it is designed to support a tissue valve which has been tanned and expanded as described above; and (2) its inner surface is anatomically configured to conform nearly exactly to the exterior surface of the valve. An ancillary distinguishing feature of an embodiment of the invention stent in which the fabric cover extends over only the exterior surface of the stent is that the cover is heat laminated directly to the stent frame thereby providing a strong, effective union between cover and frame.

BRIEF DESCRIPTION OF THE DRAWINGS

In the drawings:

FIG. 1 is an enlarged, elevational view of an embodiment of the heart valve prosthesis of this invention;

FIG. 2 is a top plan view of the heart valve prosthesis of FIG. 1;

FIG. 3 is a top plan view of the stent, without fabric covering, of the heart valve prosthesis of FIG. 1;

FIG. 4 is an exploded view showing the four basic elements of the heart valve prosthesis of FIG. 1;

DETAILED DESCRIPTION OF THE INVENTION

The valves used in the prostheses of the invention are tanned, expanded natural tissue cardiac valves. Homograft or heterograft valves may be used. For implantation in humans aortic porcine valves are preferred because they are very similar to human valves and easy to procure. Also, their uniformity (and reproducibility) may be controlled through control of the donor population. A series of porcine valves taken from donors at ages (approximate) 3 weeks, 3 months, 6 months, 1 year, and 2 years provides an excellent selection of valve sizes for use in human heart valve prostheses. These valves will range in size from about 20 to about 35 mm outside diameter.

In order to minimize the deleterious effect of autolysis and bacterial/enzymatic action of the valve tissue, the valves should be procured fresh and kept in chilled saline pending tanning. For convenience the entire aortic root is taken and tanned, and the valve is dissected from the root after tanning. It is desirable that the valves be tanned within about one-half day of their procurement; otherwise they may become flaccid and lose their normal firm texture. The tanning improves the tensile (strength) properties of the valves and improves their resistance to reactivity in vivo to body tissue and fluids. It is essential that the tanning be carried out so as to substantially maintain the natural configuration of the valve despite the tanning. It was found that this could be accomplished by using a 0.5% to 10% glutaraldehyde solution as the tanning agent and by keeping the valve expanded during the tanning. Such expansion may be effected by applying a positive pressure of about 20 mm Hg to about 100 mm Hg, preferably about 50 mm Hg to the valves. Pressure may be exerted on the valves by a hydrostatic column attached to the valve cuff, the valves being effectively sealed to maintain the pressure by closure of the valve cusps and by ligation of arteries. The time over which the valve should be kept in contact with the glutaraldehyde solution to achieve the desired degree of tanning varies with the glutaraldehyde concentration. At the above stated concentrations the valves should be kept in the solution for about ten minutes to one hour. For instance, treatment with 5% glutaraldehyde solution for approximately ten minutes at ambient temperature provided valves with good configuration maintenance.

After tanning the valves may be stored in a 0.1% to 0.8% glutaraldehyde solution to prevent them from drying out. At such concentrations glutaraldehyde also has sufficient cidal activity to keep the tanned valves sterile. Caution should be taken against storing the valves in more concentrated solutions since the same may cause the valve cusps to stiffen and thus be susceptible to in vivo failure due to stress fracture. Preferably the tanned valves are incorporated into the prostheses within about two days of their procurement.

Figure 8:
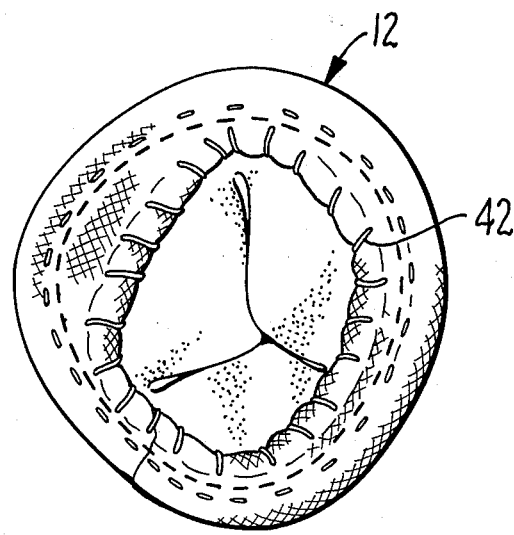
FIG. 8 is a bottom plan view of the heart valve prosthesis of FIG. 1.
Figure 9:
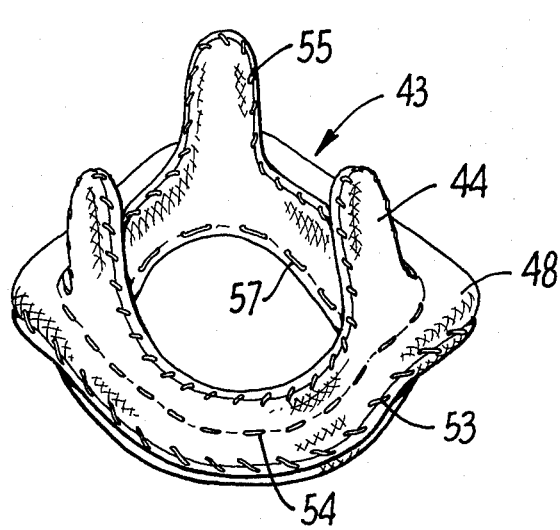
FIG. 9 is an enlarged, elevational view of a second embodiment of the heart valve stent of this invention.

FIG. 4 shows an aortic porcine valve, generally designated 11, that was taken from a pig approximately 6 months old, tanned pursuant to the above procedure, and trimmed for inclusion into a heart valve prosthesis, generally designated 12 in FIGS. 1, 2 and 8. The interior of valve 11 is comprised of three cusps or leaflets 13, 14, 15 whose bases are integral with the muscle tissue 16 that defines the aortic orifice and whose apices extend into the orifice to meet at axis 17 generally centrally (see FIG. 3) of the orifice. Cusps 13, 14, 15 are joined at commissures 18, 19, 22.

Figure 5:
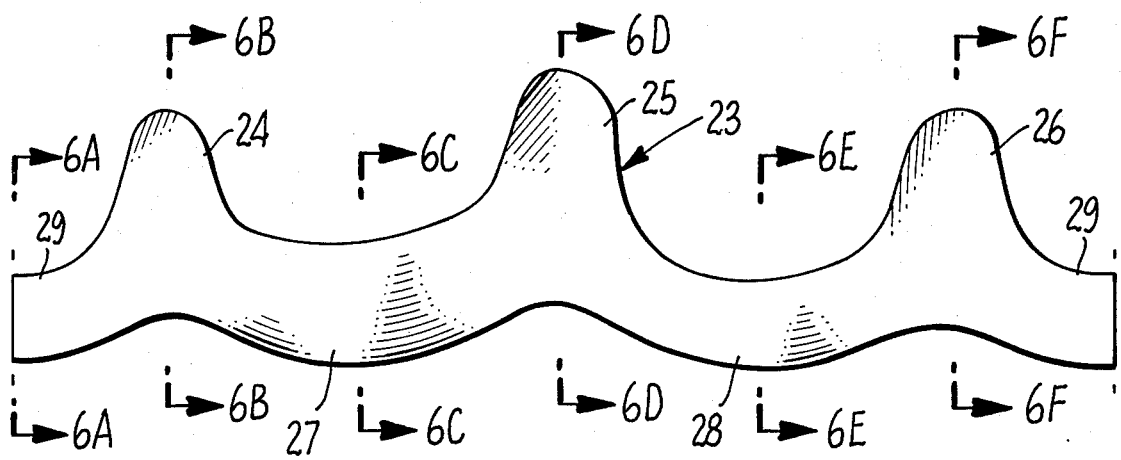
FIG. 5 is a developmental layout view of the frame of FIG. 4 approximately two times actual scale.
Figure 6:
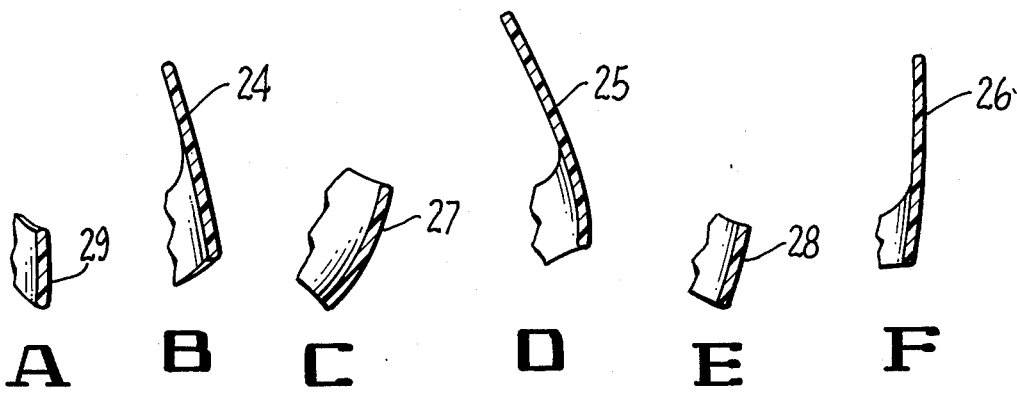
FIG. 6A is a sectional view taken along line 6A-6A of FIG. 5.
FIG. 6B is a sectional view taken along line 6B-6B of FIG. 5.
FIG. 6C is a sectional view taken along line 6C-6C of FIG. 5.
FIG. 6D is a sectional view taken along line 6D-6D of FIG. 5.
FIG. 6E is a sectional view taken along line 6E-6E of FIG. 5.
FIG. 6F is a sectional view taken along line 6F-6F of FIG. 5.

Valve 11 is supported in prosthesis 12 by a stent frame generally designated 23 and shown separately in FIGS. 3 through 6. As seen in FIGS. 3 and 4, frame 23 has an irregular ring shape and is comprised of three spaced, curved, ventricular struts or posts 24, 25, 26 interconnected by three annular, ventricularly relieved sections 27, 28, 29. The curvature of the ventricular edge 32 of frame 23 generally follows the bases of valve cusps 13, 14, 15. The atrial edge 33 of frame 23 has atrial apices and depressions that generally register with the relieved sections and struts, respectively, of ventricular edge 32. The spacing between struts 24, 25, 26 is unequal (detailed in FIG. 3) and struts 24 and 25 are biased radially inwardly (FIGS. 3, 6B and 6D). In smaller stents strut 26 tends to be generally parallel to axis 17 (FIGS. 3 and 6F), whereas in larger stents it tends to be biased radially inwardly but to a much lesser degree than struts 24, 25. Correlatively annular sections 27, 28 are biased radially outwardly FIGS. 6C and 6E), whereas annular section 29 is generally parallel to axis 17 (FIG. 6A) in the case of smaller stents and in the case of larger stents tends to be biased radially outwardly but to a much lesser degree than sections 27, 28. As shown in FIGS. 5 and 6, the respective heights of the frame struts and annular sections are unequal. The inner surface of the frame defined by annular sections 27, 28, 29 and the bases of struts 24, 25, 26 is generally convex outwardly.

The above described configuration of frame 23 is anatomically identical to valve 11. Specifically the interior configuration of frame 23 is the negative of the exterior configuration of valve 11. In this manner frame 23 provides a near perfect fit and support for valve 11. The configurations of frames made from valves taken from pigs of different ages than the pig from which valve 11 was taken will be essentially identical to the configuration of frame 23; but their sizes will be correspondingly smaller or larger than frame 23, as the case may be.

The anatomical configuration of frame 23 is achieved by molding it from a tanned, expanded valve, such as valve 11, as follows. A rubber casting of the interior of the valve is made. This casting serves as a support for the valve. The valve is then placed over the rubber casting and the valve/casting assembly is dipped into a curable liquid rubber, such as the silicone rubber sold under the trade designation Silastic RTV, to form an exterior coating on the assembly. After the coating has set the assembly is separated from the coating. The coating thus forms a mold of the exterior of the valve. From this rubber mold a rubber casting of the exterior of the valve is made. From this casting of the valve exterior a wax casting is made. Finally a metal mold of the exterior of the valve is made from the wax casting by the lost wax technique. Plastic stent frames, such as frame 23, may be made from the metal mold by injection molding.

The material from which frame 23 is made and the thickness of frame 23 may be such that frame 23 is bendable and resilient so that the struts 24, 25, 26 are able to bend radially to accommodate the in vivo movement of the valve cusps. Thermoplastic materials to which the body has little or no reactivity, such as Delrin polymer (a polyformaldehyde of greater than 15,000 molecular weight sold by DuPont), Lexan polymer (a polycarbonate), Nylon polymer (a hexamethylene diamine-adipic acid polymer), high density polyethylene and polypropylene, may be used to make the frames. The thickness of frames made of such materials will depend on the size of the valve for which the frame is made. Larger frames are used for mitral valve replacements and should be thicker than the samller frames used for aortic valve replacements. Usually the thickness will be in the range of about 0.5 to about 1.5 mm, with thicknesses in the lower end of this range being used for the smaller frames and those in the higher end for the larger frames. Frames made of Delrin polymer are preferred.

Figure 7:
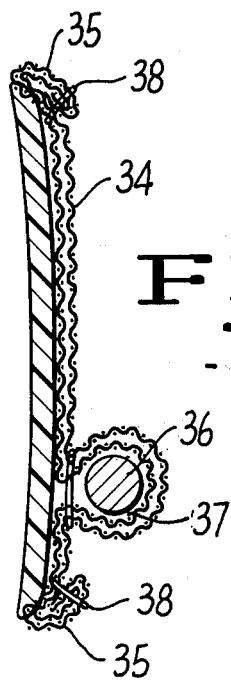
FIG. 7 is an enlarged vertical sectional view through an apical portion of the stent of the heart valve prosthesis of FIG. 1.

The exterior of frame 23 is covered by a nonabsorbent fabric cover 34 (FIGS. 4 and 7). Cover 34 inhibits thrombus formation, promotes tissue growth and endothelialization of exposed prosthetic surfaces and provides means for receiving the sutures by which valve 11 is emplaced within the stent frame. Fabric cover 23 is desirably multilayered and may be formed from available surgical woven, mesh or sponge materials. Cover 34 has a thickened portion or bead 35 around its entire perimeter which may be formed either by rolling the edge of the cover or by sewing or otherwise affixing additional material thereto. The cover 34 shown in the drawings has two layers and bead 35 was formed by rolling the edge of the layers. The material from which cover 34 is formed should be unreactive to body tissue and fluids. It is desirable to use thermoplastic materials which have a substantially higher melting point than the material from which frame 23 is made, since such materials may be readily and effectively attached to frame 23 by heat lamination.

The cover 34 shown in the drawings was attached to frame 23 as follows. Open mesh Dacron polymer (polyethylene terephthalate) cloth (No. 6050, USCI Co) was doubled and a ring 36 (FIGS. 4 and 7) was sewn into a pocket 37 formed in the cloth. Ring 36 provides a site for suturing prosthesis 12 into the heart opening. It may be made from appropriate medical grade, synthetic cloths, meshes, or felts. Dacron polymer or Teflon polymer (polytetrafluoroethylene) felt has been found to be especially useful. The doubled cloth is then positioned over the exterior of frame 23 and a heating element, eg, a soldering iron, is run slowly around the exterior perimeter of frame 23. The temperature of the heating element should be above the melt temperature of frame 23 and below the melt temperature of cover 34. This causes the material of frame 23 to melt at said perimeter and the cover to be imbedded in the molten frame material. Once the heating element is removed the molten frame material solidifies quickly thereby bonding the cover 34 to the exterior perimeter of the frame 23. The edge of the cover 34 outwardly of the bond is trimmed, rolled twice and sewn down with a thread 38 to form bead 35.

Valve 11 is assembled within frame 23 as follows. Valve 11 is first seated within frame 23 with commissures 18, 19, 22 generally lined up with frame struts 25, 26, 24 respectively. Because the interior configuration of frame 23 is substantially the negative of the exterior configuration of valve 11 the latter sits snugly within the former. The ventricular edge of valve 11 is then sutured to the bead 35 along the ventricular edge 32 of frame 23 (FIG. 2) and the atrial edge of valve 11 is similarly sutured to the bead 35 along the atrial edge 33 of frame 23 (FIG. 8) with sutures 42. Any excess muscle tissue 16 may be trimmed away during the suturing. This completes the assembly of prosthesis 12 and it is ready for implantation within a patient at any intracardiac position. Implantation procedures are well-established in the surgical art and do not require elaboration herein.

FIGS. 9-12 illustrate another heart valve stent, generally designated 43, of this invention. Stent 43 is essentially identical to the stent of FIGS. 1-8 except as regards its cloth covering 44 and the size of its frame, generally designated 45.

Figure 11:
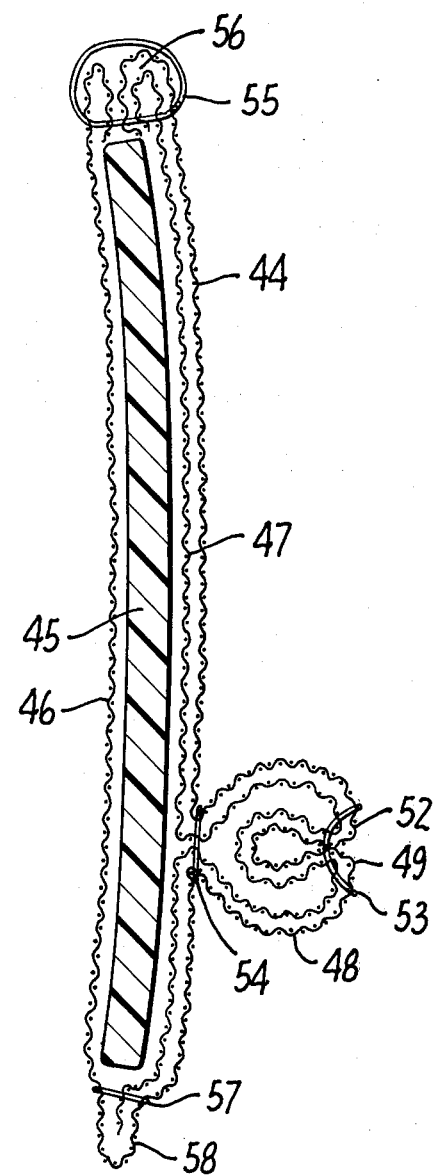
FIG. 11 is an enlarged vertical sectional view through an apical portion of the stent of FIG. 9.

As seen in FIG. 11 cloth covering 44 covers both the interior and exterior surfaces of frame 45. It comprises a first layer 46 that covers the interior and exterior surfaces of frame 45 and a second layer 47 that covers only the exterior surface of frame 45 and is located inwardly of layer 46. Layers 46, 47 are bunched to form an annular U-shaped thickened portion 48 that extends completely around frame 45. The ends 49, 52 of portion 48 are tied together by a thread 53 and the base of portion 48 is tied by another thread 54. Portion 48 serves the same purpose as ring 36 of the stent of FIGS. 1-8. Layers 46, 47 are folded and tied together by a thread 56 along the ventricular edge of frame 45 to form a ventricular bead 56 and are similarly tied together along the atrial edge of frame 45 by another thread 57 to form an atrial bead 58. Beads 56, 58 serve the same purpose as bead 35 of the stent of FIGS. 1-8. Unlike the cloth cover 34 of the stent of FIGS. 1-8, cloth cover 44 is not bonded directly to frame 45.

Figure 10:
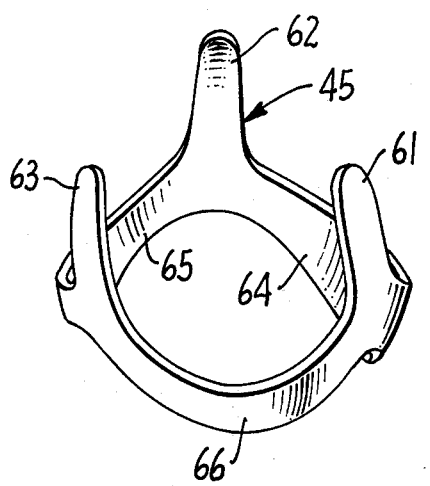
FIG. 10 is an enlarged, elevational view of the frame of the stent of FIG. 9.
Figure 12:
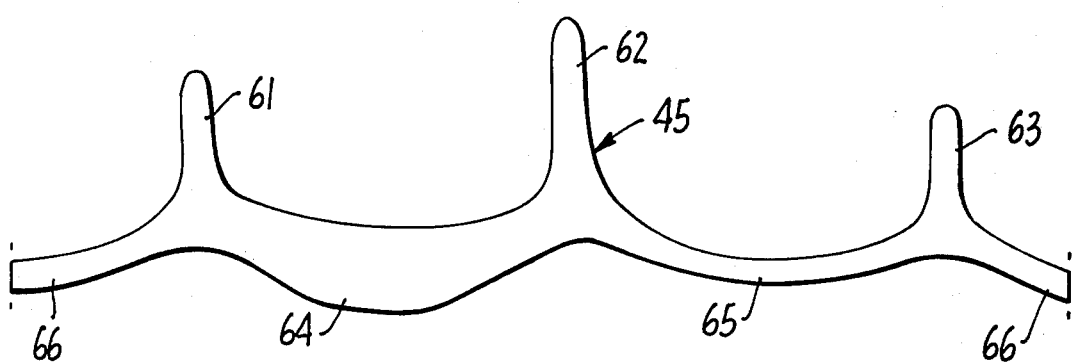
FIG. 12 is a developmental layout view of the frame of the stent of FIG. 9 approximately two times actual scale.

Referring to FIGS. 10 and 12 frame 44 has an irregular ring shape and is comprised of three spaced struts 61, 62, 63 that are interconnected by three sections 64, 65, 66. These struts and interconnecting sections have generally the same spacial attitudes and serve the same purposes as the corresponding struts and interconnecting sections of the frame of the stent of FIGS. 1-8. However, the transverse dimensions of the former are generally smaller than those of the latter. Such smaller dimensions are desirable because they make the stent lighter and less bulky. Of course the transverse dimensions of the struts and interconnecting sections should not be so small as to adversely affect the structural integrity or operation of the stent. In this regard the preferred transverse dimensions (measured at the midpoint) of the struts is 3 to 4 mm. The preferred transverse dimension (measured at its widest point) of the right coronary interconnecting section (64 in FIGS. 10 and 12, and 27 in FIGS. 4-6) will vary with the overall size of the frame, getting progressively larger as the overall size of the frame increases. For instance, in a stent for a 20 mm valve it is preferably about 5 mm, for a 24 mm valve preferably about 6.4 mm, for a 28 mm valve about 7.4 mm and so forth. Thus the transverse dimension of the right coronary interconnecting section will normally be in the range of 5 to 8 mm, depending on the overall frame size. The transverse dimension of each of the other two interconnecting sections (65, 66 in FIGS. 10-12 and 28, 29 in FIGS. 4-6) is preferably about 2 to 3 mm at its widest point.

The components of stent 43 may be made from the same materials as the components of the stent of FIGS. 1-8. Likewise frame 45 may be made in the same manner as frame 23 of the stent of FIGS. 1-8 so that it too is anatomically configured, and a valve, such as valve 11, may be assembled within stent 43 in the same manner that valve 11 is assembled within frame 23.

Modifications of the stents, prostheses and procedures for making the same described above which are obvious to those skilled in the prosthesis, surgical and polymer arts are intended to be within the scope of the following claims. Such modifications include, without limitation, the use of other materials not specifically mentioned above for the stent frame and/or fabric cover, varying the size and location of ring 36 or portion 48 to adapt the prosthesis for use as a mitral or tricuspid valve replacement, as the case may be, and, in the case of an exterior cover only, affixing the cover to the frame edge by means other than heat lamination, such as with adhesives.

We claim:

1. A stent for a tanned natural tissue heart valve prosthesis comprising:
   a. a plastic frame the interior configuration of which is substantially the negative of the configuration of the exterior of said valve; and
   b. a fabric cover covering at least the exterior surface of the frame.

2. The stent of claim 1 including:
   c. means along the frame perimeter providing a site for attaching the valve to the stent.

3. The stent of claim 2 wherein said means is a thickened portion of the cover.

4. The stent of claim 2 wherein said means comprises a rolled edge of the cover.

5. The stent of claim 1 wherein the cover includes a thickened annular exterior portion providing a site for attaching the prosthesis intracardially.

6. The stent of claim 1 wherein the frame has an irregular ring shape and comprises three unequally spaced ventricular struts of unequal height, two of which are biased radially inwardly and the third of which is biased radially inwardly but to a lesser degree than the other two or is generally parallel to the frame axis and three annular ventricular relieved portions integral with and respectively interconnecting said struts, said portions being of unequal height, two of which are biased radially outwardly and the third of which is biased radially outwardly but to a lesser degree than the other two or is generally parallel to the frame axis, the inner surface of the frame defined by the inner surfaces of the bases of said struts and the inner surfaces of said portions being generally convex outwardly.

7. The stent of claim 1 wherein the portion of said cover covering said exterior surface is multilayered.

8. The stent of claim 1 wherein the cover covers only the exterior surface of the frame and is affixed to the frame along the exterior perimeter thereof.

9. The stent of claim 8 wherein the material forming said cover is a thermoplastic having a substantially higher melt temperature than said frame and said cover is affixed to the frame by heat lamination.

10. The stent of claim 1 wherein the cover covers the entire surface of the frame.

11. The stent of claim 1 wherein the thickness of said frame is about 0.5 to about 1.5 mm.

12. The stent of claim 1 wherein said frame is formed of Delrin polymer and said cover is formed of Dacron polymer.

13. The stent of claim 1 including:
c. means along the frame perimeter providing a site for attaching the valve to the stent and wherein the cover covers the entire surface of the frame and includes a thickened annular exterior portion providing a site for attaching the prosthesis intracardially, the thickness of the frame is about 0.5 to about 1.5 mm and the frame has an irregular ring shape and comprises three unequally spaced ventricular struts of unequal height having a transverse midpoint width of 3 to 4 mm, two of which are biased radially inwardly and the third of which is biased radially inwardly but to a lesser degree than the other two or is generally parallel to the frame axis, and three annular ventricular relieved portions integral with and respectively interconnecting said struts, said portions being of unequal height with the right coronary portion having a transverse dimension at its widest point of 5 to 8 mm and the other two portions having a transverse dimension at their widest points of 2 to 3 mm, two of the portions being biased radially outwardly and the third being biased radially outwardly but to a lesser degree than the other two or being generally parallel to the frame axis, the inner surface of the frame defined by the inner surfaces of the bases of said struts and the inner surfaces of said portions being generally convex outwardly.

14. A heart valve prosthesis comprising:
a. the stent of claim 1; and
b. a tanned natural tissue heart valve affixed within said stent.

15. The heart valve prosthesis of claim 14 wherein the valve was tanned with glutaraldehyde in an expanded state.

16. The heart valve prosthesis of claim 14 wherein the valve was tanned with a 0.5% to 10% glutaraldehyde solution under a pressure of about 20 to about 100 mm Hg.

17. The heart valve prosthesis of claim 14 wherein the valve was tanned with a 5% glutaraldehyde solution under a pressure of about 50 mm Hg.

18. The heart valve prosthesis of claim 14 wherein the valve is a porcine aortic valve.

19. A heart valve prosthesis comprising:
a. the stent of claim 2; and
b. a tanned natural tissue heart valve affixed within said stent.

20. A heart valve prosthesis comprising:
a. the stent of claim 6; and
b. a tanned natural tissue heart valve affixed within said stent.

21. A heart valve prosthesis comprising:
a. the stent of claim 10; and
b. a tanned natural tissue heart valve affixed within said stent.

22. A heart valve prosthesis comprising:
a. the stent of claim 13; and
b. a tanned natural tissue heart valve affixed within said stent.

23. The heart valve prosthesis of claim 22 wherein the valve is a porcine aortic valve tanned with glutaraldehyde in an expanded state.

24. The heart valve prosthesis of claim 23 wherein the valve is a porcine aortic valve tanned with a 0.5% to 10% glutaraldehyde solution under a pressure of about 20 to about 100 mm Hg.

* * * * *